(12) United States Patent
Forman et al.

(10) Patent No.: US 10,275,907 B2
(45) Date of Patent: Apr. 30, 2019

(54) METHOD AND SYSTEM OF MANAGED IMAGE RECONSTRUCTION IN MEDICAL IMAGING

(71) Applicant: Siemens Healthcare GmbH, Erlangen (DE)

(72) Inventors: Christoph Forman, Erlangen (DE); Rainer Kirsch, Baiersdorf (DE); Christian Muehlhaeusser, Pretzfeld (DE); Edgar Mueller, Heroldsbach (DE); Peter Speier, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 59 days.

(21) Appl. No.: 15/341,195

(22) Filed: Nov. 2, 2016

(65) Prior Publication Data

US 2017/0124730 A1  May 4, 2017

(30) Foreign Application Priority Data

Nov. 2, 2015 (DE) .................. 10 2015 221 405

(51) Int. Cl.
| | | |
|---|---|---|
| *G06K 9/00* | (2006.01) | |
| *G06T 11/00* | (2006.01) | |
| *G06F 19/00* | (2018.01) | |
| *G06T 7/00* | (2017.01) | |

(52) U.S. Cl.
CPC ............ *G06T 11/003* (2013.01); *G06F 19/00* (2013.01); *G06F 19/321* (2013.01); *G06T 7/0012* (2013.01); *G06T 11/006* (2013.01); *G06T 2207/10081* (2013.01); *G06T 2207/10088* (2013.01); *G06T 2211/428* (2013.01)

(58) Field of Classification Search
CPC ................ G06F 19/321; G06T 11/003; G06T 2207/10081; G06T 2207/10088; G06T 7/0012
See application file for complete search history.

(56) References Cited

PUBLICATIONS

Serrano et al. ("Towards QoS-Oriented SLA Guarantees for Online Cloud Services", 2013).*
Meng et al. ("Ultrafast and scalable cone-beam CT reconstruction using MapReduce in a cloud computing environment", 2011).*
Meng, Bowen, Guillem Pratx, and Lei Xing. "Ultrafast and scalable cone-beam CT reconstruction using MapReduce in a cloud computing environment." Medical physics 38.12 (2011): 6603-6609.*
Serrano, Damián, et al. "Towards qos-oriented sla guarantees for online cloud services." Cluster, Cloud and Grid Computing (CCGrid), 2013 13th IEEE/ACM International Symposium on. IEEE, 2013.*
Alakeel, Ali M. "A guide to dynamic load balancing in distributed computer systems." International Journal of Computer Science and Information Security 10.6 (2010): 153-160.*

(Continued)

*Primary Examiner* — Avinash Yentrapati
(74) *Attorney, Agent, or Firm* — Schiff Hardin LLP

(57) ABSTRACT

The invention concerns a method for reconstructing medical image data which has access to free capacities of at least two computers and manages the use thereof for the purposes of the reconstruction. The method is a particularly reliable alternative to the reconstruction of medical image data based on algorithms that would require a working memory of above-average size.

13 Claims, 5 Drawing Sheets

(56) References Cited

PUBLICATIONS

Meng et al., "Ultrafast and scalable cone-beam CT reconstruction using MapReduce in a cloud computing environment," Med. Phys., vol. 38 (12), pp. 6603-6609 (2011).
"Cloud computing," Wikipedia, pp. 1-8.
Xue et al., "Distributed MRI Reconstruction Using Gadgetron-Based Cloud Computing," Magnetic Resonance in Medicine, vol. 73, pp. 1015-1025 (2015).
Yarra, ktblock.de/yarra, p. 1.
Framework Boinc, boinc.berkeley.edu/.
Boinc—Project Seti, setiathome.ssl.berkeley.edu.
Serrano et al., "Towards QoS-Oriented SLA Guarantees for Online Cloud Services," 13th IEEE/ACM International Symposium, pp. 50-57 (2013).

* cited by examiner

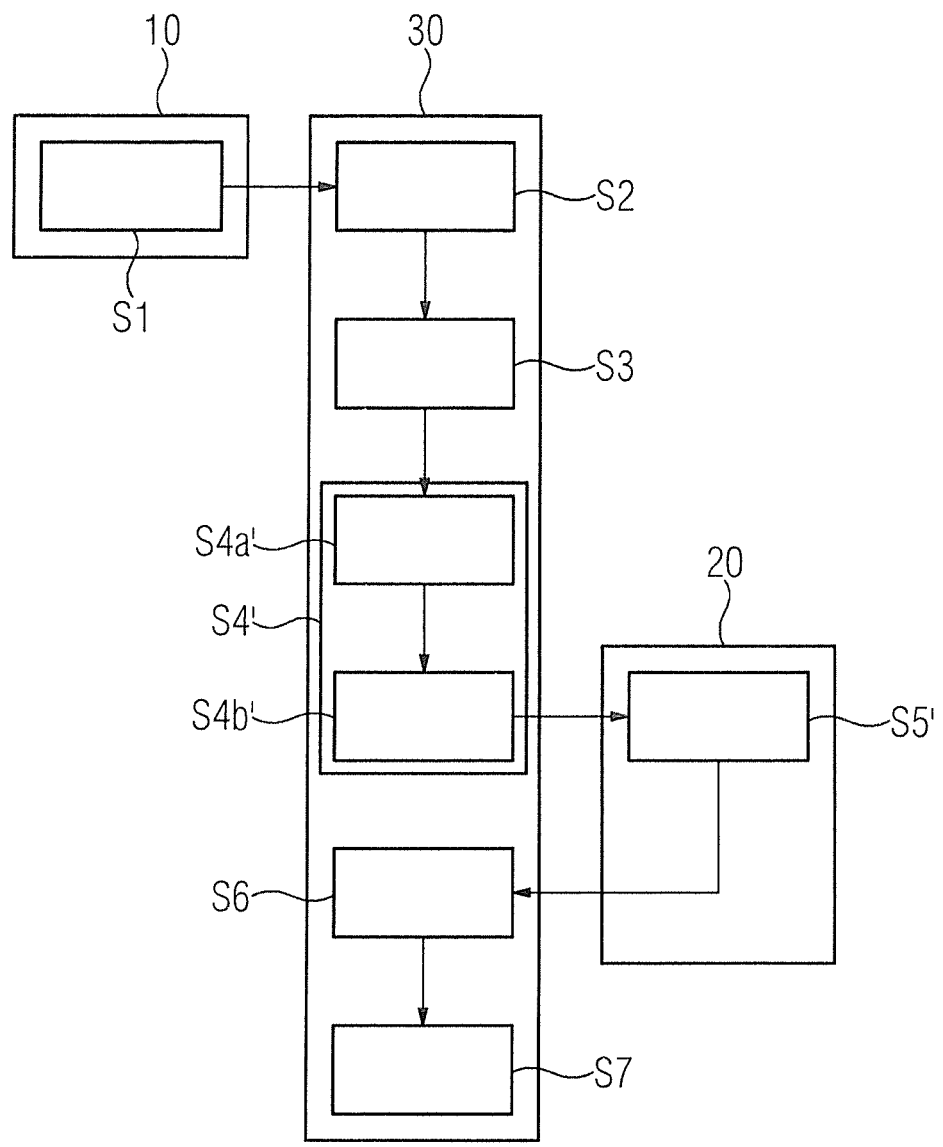

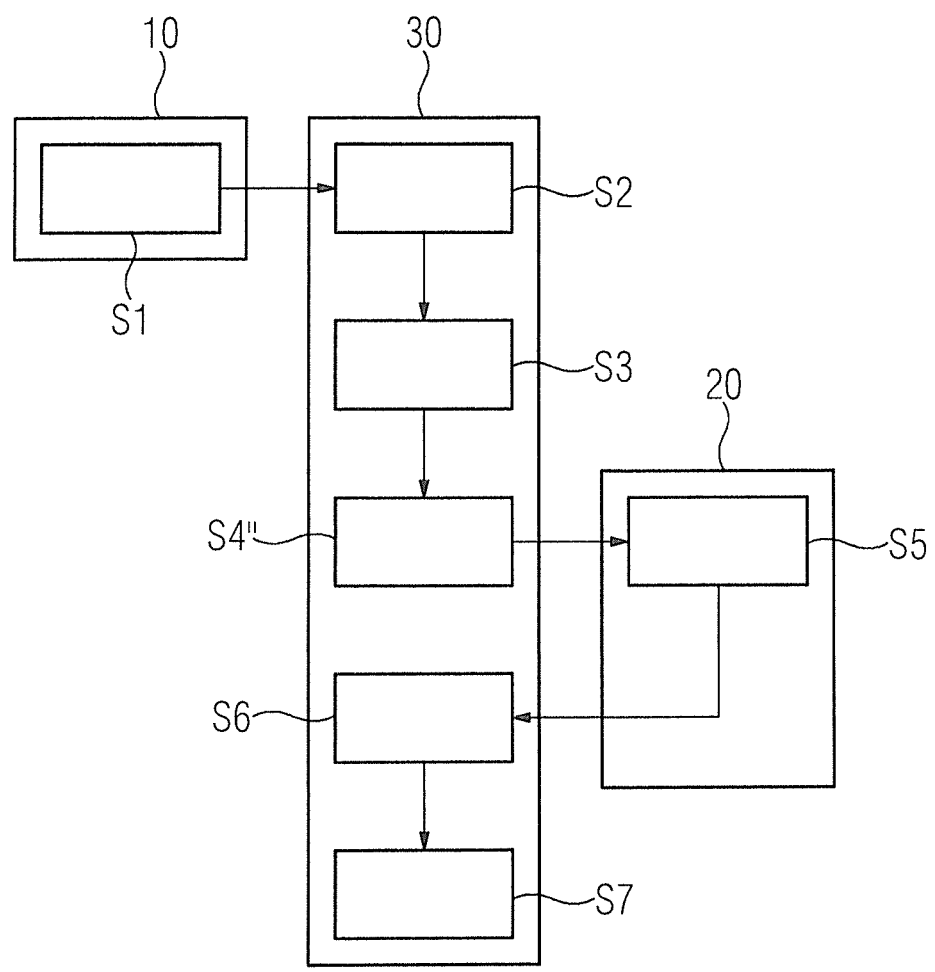

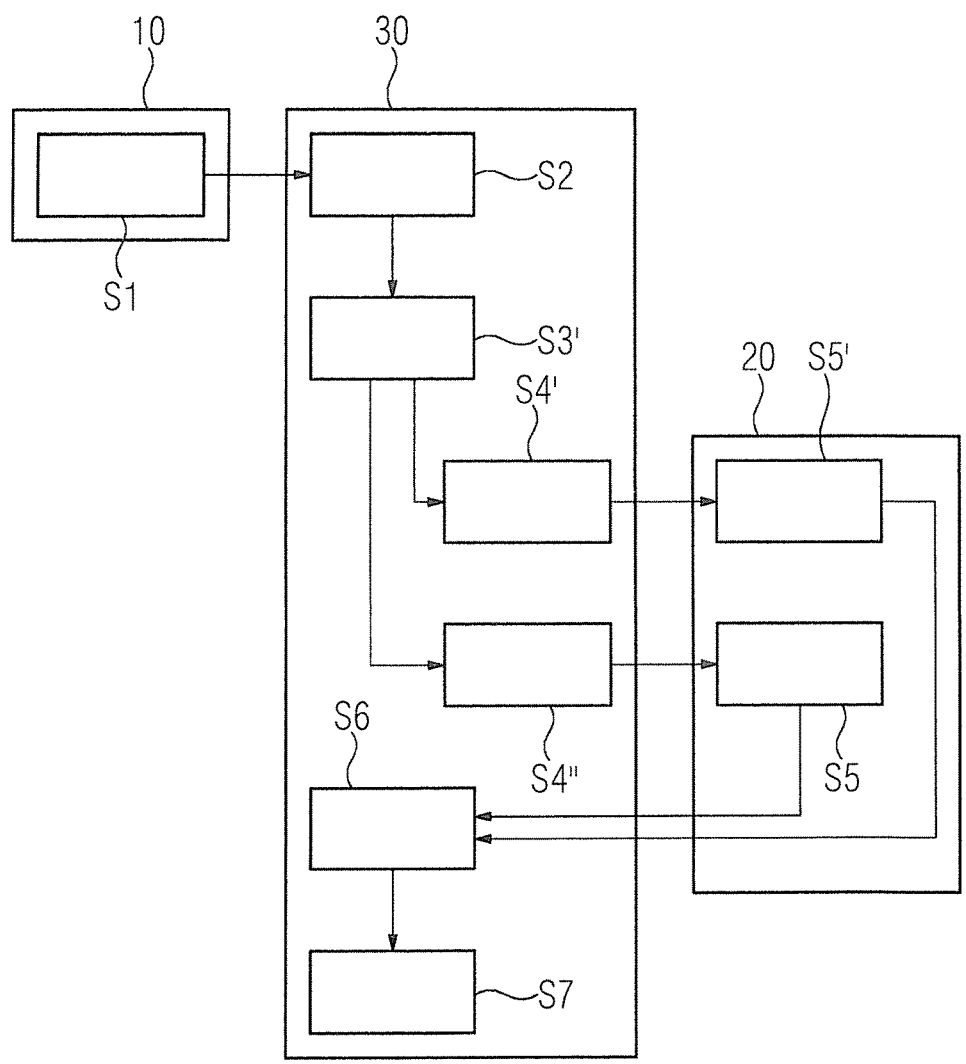

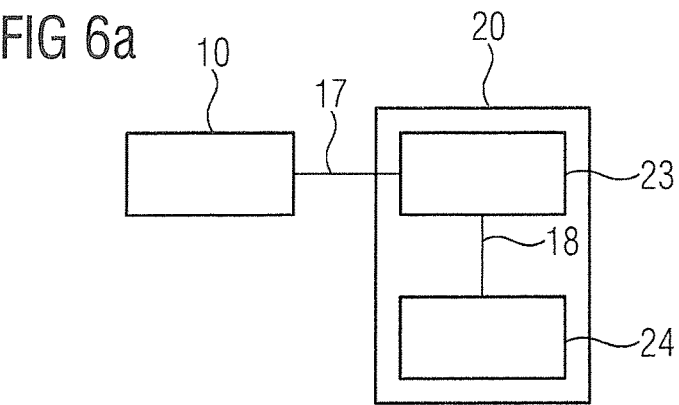
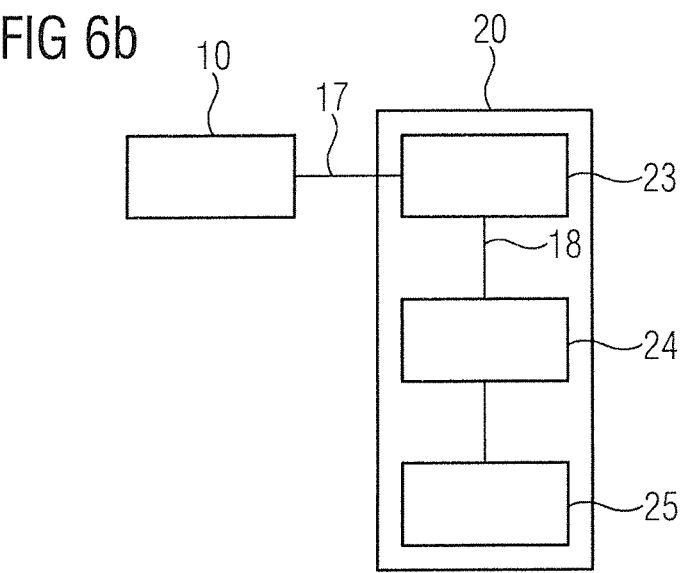
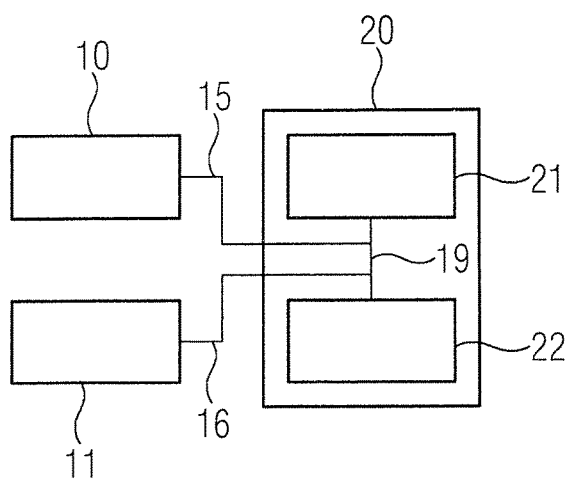

METHOD AND SYSTEM OF MANAGED IMAGE RECONSTRUCTION IN MEDICAL IMAGING

BACKGROUND OF THE INVENTION

Field of the Invention

The present invention concerns a method for reconstructing medical image data. The present invention further concerns a system configured to perform such a method, and a non-transitory, computer-readable data storage medium encoded with programming instructions that cause a computer or computer system to execute such a method.

Description of the Prior Art

The generation of medical image data on the basis of raw data acquired by a medical imaging device, such as a magnetic resonance apparatus, is computationally intensive and imposes heavy demands on the computers that perform such calculations. The aim of new acquisition and reconstruction strategies, such as iterative reconstruction for example, is to acquire smaller quantities of raw data than has traditionally been the case and to achieve an equal or better quality of image data with the use of new reconstruction algorithms. Alternatively, this also enables the quality of the image data to be increased while the quantity of the acquired raw data remains the same. The advantages of acquiring a smaller volume of data are different for different imaging modalities. In computed tomography, the applied energy dose can correlate with the data volume, in magnetic resonance tomography the acquisition time. In both cases, a reduction in the amount of data is advantageous. In contrast to the conventional reconstruction algorithms, these new algorithms are orders of magnitude more computationally intensive and place considerably higher demands on the working memories of the computers that perform said algorithms. It is desirable to complete the reconstruction of the image data within the shortest possible length of time and to provide said image data to an image viewing module in order to facilitate a smooth clinical workflow. This calls for computers that are capable of satisfying the high demands of the new algorithms.

Commercial medical imaging devices are equipped among other components with a computer that processes the acquired raw medical data of precisely the medical imaging device and usually is also spatially associated with that device. The performance of the computer is dimensioned such that it is capable of running the algorithms required by the medical imaging device on all the acquired raw data. Accordingly, the length of time required for executing the algorithm is precisely determined. Since there are strong variations in both the amount of data and the demand imposed by the algorithms on the processing power of the computer, the capacity of the computer is oftentimes utilized only to a limited extent, or even not at all if, for example, the medical imaging device is not in operation.

It is known that particularly computationally intensive algorithms are not performed on computers that are associated directly with the medical imaging device, but use external computers.

Yarra (ktblock.de/yarra) and Meng et al. (Ultrafast and scalable cone-beam CT reconstruction using MapReduce in a cloud computing environment, in Med. Phys. 2011, 38:6603-6609) provide as one embodiment of the method that different medical imaging devices have one or more shared computers with high computing capacity at their disposal and can access the same as necessary.

A further possibility is to lease computing capacities from commercial service providers (Cloud computing, de.wikipedia.org/wiki/Cloud_Computing).

The use of free capacities of a number of computers can furthermore be controlled by the BOINC framework (boinc.berkeley.edu/). BOINC is used by the SETI@home project (setiathome.ssl.berkeley.edu/), for example.

SUMMARY OF THE INVENTION

An object of the invention is to provide a method for reconstructing medical image data that has access to free capacities of at least two computers and efficiently manages the use thereof for the purposes of the reconstruction. It is furthermore an object of the invention to provide a system, and a computer-readable data storage medium that are designed to perform the method.

The inventive method for reconstructing medical image data includes the following steps.

Raw medical data of an examination subject are acquired by operation of a first medical imaging device that is connected via an interface to a computer group having at least two computers. A computing management computer is provided that is connected to the computer group and to the first medical imaging device. The computing management computer ensures that a guaranteed minimum performance is maintained for the reconstruction of medical image data. The free capacities of the computers of the computer group are checked by the computing management computer before assigning the raw medical data to the computer group for processing, while maintaining the guaranteed minimum performance. The computing management computer manages the merging of the processed raw medical data and the provisioning of the medical image data.

The examination subject can be a patient, a training volunteer or a phantom. A medical imaging device has a control computer that manages the acquisition of the raw medical data from the examination subject. The medical imaging device additionally has an interface to a computer group having at least two computers that are connected to one another. The medical device is accordingly connected to the computers of the computer group. The working memory of each computer is determined by the given hardware and can be used for accomplishing tasks such as calculations of predetermined algorithms, for example. A part of the working memory can also be used for internal tasks of the computer which guarantee its functionality. Generally, tasks are temporary and the use of the working memory is subject to change over time. The part of the working memory that is not used for performing tasks is unused and contributes to the free capacity of the computer.

A common feature of the computers of the computer group is that they can have free capacities when they are not being accessed by the computing management computer. They typically differ from one another by virtue of the reasons for their procurement and the associated primary tasks that are fulfilled by these computers. Computers of the computer group can be used by medical personnel primarily for the visualization of medical image data or for management tasks, or may have been purchased as part of a medical imaging device, such as in order to perform the processing of the raw medical data of said medical imaging device, or may have been purchased for the purpose of performing tasks assigned to them by the computing management computer.

Medical image data can be images representing an anatomy of an examination subject. Furthermore, medical image data may also contain quantitative information relating to the anatomy of an examination subject that can be provided for visualization purposes in the form of two- or three-dimensional maps. Equally, medical image data can represent the anatomy for example in segmented form, which may contain information relating to limits of functional entities inside the patient.

The processing of raw medical data is a step in the generation of medical image data from raw medical data. Depending on the extent of the medical image data, the processing can describe a step in the reconstruction of the medical image data or further steps that, for example, include the generation of quantitative maps. Additional tasks, such as motion correction, can also be taken into consideration during the processing of raw medical data.

The processing of raw medical data may also include postprocessing steps following on from the reconstruction, such as a segmentation of functional entities inside a patient, for example. Further post-processing steps which evaluate the reconstructed medical image data or combine with further information that is provided are possible. Generally, more working memory is required for the processing of raw medical data than exclusively for the visualization of the already reconstructed medical image data.

The method according to the invention uses a computing management computer that is designed (programmed or configured) for controlling the processing of the raw medical data and the reconstruction of the medical image data.

The computing management computer is typically programmed by software and the method can be implemented as an algorithm on at least one of the following computers: a computer of the computer group and the control computer of the first medical imaging device. The computing management computer is connected to the computer group and the medical imaging device. The computing management computer guarantees that a minimum performance will be maintained during the reconstruction of the medical image data. In this case the performance is described by means of a parameter which quantifies the capability to perform the reconstruction of the medical image data. The quantification can be performed on the basis of a variety of factors, such as the length of time required for the reconstruction of the medical image data, or the minimum capacity of the computer group that can be used for the reconstruction of the medical image data.

A medical imaging device generally has a number of techniques at its disposal for acquiring sets of raw medical data which, depending on imaging modality, can differ from one another to varying degrees. Different techniques for acquiring the data can also be assigned different techniques for processing the raw medical data, in particular different reconstruction tasks. The demands imposed on the working memory of the computer can be determined by the type of reconstruction task, as well as by the amount of raw medical data that is to be processed. The guaranteed minimum performance may be identical for each reconstruction task of the medical imaging device or may be dependent on the amount of raw medical data and/or on the reconstruction task. The guaranteed minimum performance can be defined on a one-time basis by the user or be redefined for each reconstruction task and communicated to the computing management computer. Alternatively, the computing management computer can determine the guaranteed minimum performance as a function of the amount of raw medical data and/or the reconstruction task.

The computing management computer checks the free capacities of the computers of the computer group. This process is intended to establish on which computer or computers sufficient free capacity is available for processing the raw medical data while ensuring the guaranteed minimum performance. For this purpose the computing management computer knows the demands imposed on the working memory by the reconstruction task or determines said demands. The computing management computer decides how the free capacities of the computers are to be used and performs the assignment of the raw medical data in accordance with the decision. It may be that the raw medical data is not assigned to the computer or computers of the computer group in the originally acquired form, but is modified or processed prior to being assigned by the computing management computer or the medical device. This can be the cause when different processing steps are performed on different computers of the computer group. The computing management computer manages the processing of the raw medical data into medical image data.

If the processing of the raw medical data takes place on a single computer of the computer group, the processing can be performed in its entirety on that computer, i.e. the reconstruction of the image data can be completed in one step, the provisioning of the data being managed by the computing management computer. The merging of the processed image data is redundant in this case.

Alternatively, the raw medical data can be processed such that further steps in addition to the actual processing are necessary in order to generate medical image data. Said further steps can comprise for example the assignment of the raw medical data to a plurality of computers of the computer group and are managed by the computing management computer. This approach preferably applies when the processing of the raw medical data is carried out on different computers of the computer group.

Independently of the processing, the computing management computer manages the provisioning of the medical image data. The provisioning of the medical image data can be the storage of the medical image data in a memory of a computer and/or the display of the medical image data monitor. The management of the provisioning of the medical image data by the computing management computer can entail carrying out the provisioning of the medical image data by the computing management computer or initiating the carrying out of the provisioning of the medical image data.

Due to the guarantee of a minimum performance, it is possible to predict the maximum length of time that is required for the reconstruction of the medical image data. If the minimum performance is not defined directly by way of the maximum length of time required for the reconstruction of the medical image data, the computing management computer can determine the time on the basis of the knowledge relating to the minimum performance, the corresponding specifications of the computer group and the demands imposed by the reconstruction task on the working memory.

This has the advantage for the user that the maximum examination time of an examination subject can be predicted and consequently a reliable schedule can be produced for the medical equipment. If necessary, the timeline for the patient examinations can also be tailored to match the demands on the computer group and the sequence of the acquisition of the raw medical data or the patient sequence can be adapted.

It should be noted that the invention is not limited to the case where the computer group is connected to just one first medical imaging device and processes the latter's raw medical data in order to generate image data. Rather, a second medical imaging device can also be present and be used in addition for acquiring raw medical data of an examination subject. The second medical imaging device is connected to the computer group via a second interface and the computing management computer is connected to the second medical imaging device. The computing management computer assigns the raw medical data acquired by means of the second medical imaging device to the computer group for processing while maintaining the guaranteed minimum performance. The guaranteed minimum performance in this case can be a constant that is valid for all raw medical data and imaging devices, or a parameter that may be dependent on other factors such as the medical imaging device, the reconstruction task or the volume of raw medical data, and can be determined manually by the user or automatically by the computing management computer.

The raw medical data includes all of the data acquired by operation of the first and the second medical imaging devices that have not yet been reconstructed in their entirety into image data.

The extent of the image data to be reconstructed in this case can be specified by the user or by an algorithm, and so it can occur that an examination subject is examined first by operation of the first and then by operation of the second medical imaging device, and the raw medical data of both medical imaging devices are required for the reconstruction of the medical image data.

Equally, raw medical data acquired by operation of the first and the second medical imaging devices can originate from different examination subjects. Accordingly, the portion of the raw medical data recorded by the first medical device is independent of the portion recorded by the second medical device, and the computing management computer can take this into account when assigning the raw medical data to the computer group.

In addition to the second medical imaging device, further medical imaging devices can be connected to the computer group and the computing management computer. The further medical imaging devices are also designed for acquiring raw medical data. Typically, most or all of the medical imaging devices of the clinical operations facility are connected to the computer group. Depending on the size of the clinical operations facility, this can mean that a few individual medical imaging devices, or as many as a hundred such devices, are connected to the computer group and the computing management computer. The more medical imaging devices are networked together, the more reconstruction tasks can be processed by the computing management computer by use of the computer group.

Many sets of raw medical data are acquired independently of one another in time and place demands of differing degrees on the required working memory. Preferably the latter is configured larger in size for a greater number of medical devices than for a smaller number. It may be the case that all of the medical imaging devices connected to the computer group complete the acquisition of raw medical data simultaneously and the reconstruction thereof into medical image data is disproportionately computationally intensive and consequently imposes disproportionately high demands on the working memory. The computing management computer assigns the reconstruction tasks to the computers of the computer group while ensuring the guaranteed minimum performance. However, it is more likely that not all of the medical imaging devices complete the acquisition of raw medical data at the same time, and the reconstruction thereof into medical image data will not be disproportionately computationally intensive. In this case, due to the presence of the computer group, freer capacities are available than are necessary in order to ensure the minimum guaranteed performance, and reconstruction tasks can be completed faster than is ensured by the guaranteed minimum performance.

This advantage of the shared capacity of the computer group increases as more medical imaging devices are connected to the computer group. Since providing computers with large working memory is cost-intensive, the improved and more efficient use of working memory achieved by the computing management computer is advantageous. It is furthermore conceivable that the provided computing capacity increases less than linearly with the number of medical devices or less than linearly with the demands of the reconstruction tasks on the capacity of the computers.

According to a further embodiment of the invention, if at least two medical imaging devices are present, these can be different imaging modalities. Examples of such imaging modalities are computed tomography systems, magnetic resonance devices, angiography systems, ultrasound systems, positron-emission tomography systems, and single-photon emission computed tomography systems (SPECT).

Since medical imaging devices of different modalities are often present within a clinical facility, the option of combining different medical imaging devices enables a higher number of medical imaging devices to be connected to the computer group. As a result, the user can benefit to a greater extent from the improvement achieved by means of the computing management computer in the use of the provided computing capacity, which leads to shorter reconstruction times and/or a reduction in the capacity requiring to be provided by the computer group, and consequently to lower costs. Also conceivable is a hybrid examination of an examination subject, i.e. the acquisition of raw medical data by means of a first and a second medical imaging device, where the two medical imaging devices belong to different modalities, for example to magnetic resonance tomography and to positron-emission tomography. The shared processing of the thus acquired raw medical data allows hybrid scans even though no combined magnetic resonance/positron-emission tomography system is present.

The computing management computer is preferably designed to divide the raw medical data into a number of data packets such that each of the data packets contains subsets of the raw medical data. The computing management computer can assign the data packets as self-contained units to different computers of the computer group and manage partial reconstructions of the data packets on the individual computers, with at least one of the following aspects being taken into account:
 matching of the data packets to the capacities of the computers of the computer group according to their processing requirements,
 a priority assigned to the reconstruction of medical image data,
 number of examination subjects for which raw medical data is available,
 number of medical imaging devices by means of which the raw medical data is recorded,
 acquisition method by means of which the raw medical data is acquired,
 number of computers in the computer group.

The raw medical data can be available to the computing management computer in a variety of forms, including as a function of the number of medical imaging devices by means of which said data is recorded. The computing management computer can divide the raw medical data and gather it into data packets containing subsets of the raw medical data so that said data packets can be transferred via the interface of the medical imaging device or the interfaces of the medical imaging devices to the computer group in order to be processed by the latter. In addition to the subset of the raw medical data, the data packets can contain information on required processing steps for said subset and on the corresponding algorithms. Consequently, each data packet is a self-contained entity that contains all of the information required for the reconstruction task and can be processed on a computer of the computer group. The processing step contributes toward the reconstruction of the medical image data and is referred to as a partial reconstruction. The merging of the partially reconstructed raw medical data and the provisioning of the medical image data are managed by the computing management computer.

The computing management computer can divide the raw medical data in accordance with a variety of aspects which can be weighted by the user or be predefined. The processing requirements imposed by a data packet on the capacities of the computers can be determined by the volume of the data and/or the associated algorithm for processing the data. The computing management computer can perform a division matched to the free capacities of the computers of the computer group according to said processing requirements. A further aspect which can affect the division of the data is the priority assigned to the reconstruction of specific medical image data. The priority can be determined for example by the user, by the computing management computer, by the imaging modality by which the raw medical data were acquired, or by the time of acquisition. The priority can influence or permanently predefine the order of the reconstruction tasks, depending on further aspects that the computing management computer takes into account.

The division of the raw medical data into data packets can be determined not only by the volume of the raw medical data, but also by the number of examination subjects or the number of medical imaging devices by means of which the raw medical data are acquired. A further aspect is the acquisition method by which the raw medical data are recorded. This can relate to the imaging modality, as well as to a technique that can be performed with an imaging modality. The different sequences in magnetic resonance tomography are an example of the latter. The division into data packets may also be based on the number of computers in the computer group. The computing management computer can assign one data packet or multiple data packets to each computer.

A particularly efficient division into data packets can be achieved when the time taken for all reconstruction tasks is minimized. Alternatively, the computing management computer, while ensuring the guaranteed minimum performance, can utilize the capacities of the computers of the computer group uniformly or guarantee in addition that reconstruction tasks that are disproportionately computationally intensive and require a disproportionately large free capacity can be performed at any time. Depending on the choice of the above-cited aspects, this can be controlled by the computing management computer.

In a further embodiment of the invention, the computing management computer is designed to assign the raw medical data that is required for the reconstruction of a single medical image to a single computer of the computer group, which computer processes the raw medical data. This is advantageous when the raw medical data originates from one examination subject and are acquired by operation of one medical imaging device. With this inventive embodiment, the size of the reconstruction task is limited by the maximum free capacity that a computer of the computer group has. In this case the computing management computer can assign the raw medical data and the algorithm for the processing to the computer as a data packet. Method steps for merging the processed are unnecessary and the medical image data can be provided directly by the computer performing the reconstruction, or the computing management computer handles the provisioning.

In a further embodiment of the invention, the computing management computer, after having checked the capacities of the computers in the computer group, makes a decision as to whether the raw medical data, having been subdivided and assembled into at least two data packets, are assigned to more than one computer of the computer group, or whether the raw medical data are assigned to one computer which performs the processing in its entirety. This active decision step can ensure that all options for the reconstruction of the image data are considered and the desired optimization (e.g. reconstruction time or maximum utilization of the capacity of the computer group) is realized in an optimum manner. In particular, reconstruction tasks that demand a high capacity can be assigned by preference to a plurality of computers by the computing management computer, whereas reconstruction tasks requiring an average or less than average capacity are processed on one computer.

The method according to the invention can be implemented such that, in comparison with a second computer of the computer group, a first computer of the computer group is assigned more directly to the first medical imaging device and the first computer is designed to perform the processing of the raw medical data recorded by the first medical device without the involvement of the computing management computer. This is applicable, for example, when the first medical imaging device has at its disposal a reconstruction computer that is capable of performing the reconstruction of the medical image data even in the absence of the computer group. The first computer is connected to the first medical imaging device via a first interface. The first computer is typically part of the equipment configuration of the first medical imaging device and was purchased in conjunction with the latter for the purpose of reconstructing its medical image data.

By integrating the first computer into the computer group, the computing management computer can assign reconstruction tasks of a second medical imaging device to the first computer and thus increase the utilization of its capacity.

In another embodiment of the invention, the computing management computer assigns the processing of raw medical data recorded by the first medical imaging device to the first computer. This is possible as long as the first computer has sufficient free capacity to perform the reconstruction of the medical image data of the first medical device. The method is advantageous because there is no need to divide the raw medical data into data packets and said data is assigned directly to the first computer via the first interface.

In a further embodiment of the invention, the computing management computer assigns no raw medical data to the first computer while the first computer is processing raw medical data of the first medical imaging device. The at least one other computer of the computer group can then be used for reconstruction tasks on raw medical data of other medical imaging devices while maintaining the guaranteed minimum performance. The time calculated for this task prior to commencement of the processing of the raw medical data of the first medical imaging device is not modified by the occurrence of a further reconstruction task, even if the performance required for the processing of the raw medical data of the first medical imaging device exceeds the guaranteed minimum performance. The reconstruction task of the first medical imaging device is given precedence as a result. This accordingly provides the user of the first medical imaging device with an improved ability to plan ahead.

In a further embodiment of the invention, the computing management computer interrupts the processing of the raw medical data assigned to the first computer for processing if the latter's capacity is required for processing raw medical data of the first medical imaging device. The computing management computer can continue the interrupted processing on another computer of the computer group or on the first computer once beginning processing of the raw medical data of the first medical imaging device. This method is advantageous when raw medical data acquired by the second medical imaging device, or by a number of medical imaging devices, are processed on the first computer and utilize part or all of its capacity. In the event of the processing of the raw medical data assigned to the first computer being interrupted, the computing management computer makes sure that the guaranteed minimum performance is maintained and chooses how to proceed for the further processing.

An example to illustrate the method is that the processing of raw medical data can take place on the first computer at a higher level of performance than the guaranteed minimum performance, even though the computer group has further free capacities available to support the processing while maintaining the guaranteed minimum performance. These capacities can be accessed in the event of the first computer being required for reconstruction tasks of the first medical imaging device. The precedence given to the raw medical data of the first medical imaging device affords the user of the first medical device better ability to plan ahead.

In another embodiment of the invention, the computing management computer has a planning module (processor) that checks the free capacities of the computers of the computer group prior to commencement of the acquisition of the raw medical data and specifies the subsequent assignment to the computers of the computer group after the acquisition of the raw medical data has been completed.

The planning module is programmed by software and can be integrated as an algorithm into the computing management computer and/or can be implemented by at least one of the following computers: a control computer of a medical imaging device or a computer of the computer group. The thus configured computing management computer is embodied for obtaining knowledge about the acquisition of the raw data at an early stage and coordinating the corresponding reconstruction task or the corresponding reconstruction tasks while taking the free capacities into account already prior to the acquisition of the raw medical data. If there is more than one reconstruction task, the division into data packets can preferably be performed taking into account the raw medical data that is still to be acquired and still to be processed. A better utilization of the capacity of the computer group can be achieved as a consequence.

The planning module can furthermore be designed to take into account the time at which the acquisition of the raw medical data is expected to be completed. Depending on the modality of the medical imaging device, for example in magnetic resonance tomography, the length of time taken to acquire the raw medical data can exceed by a multiple the time taken for the processing of the raw medical data. In this case it is advantageous for the planning module to take the variation with time into account and predictively coordinate the processing of the raw medical data.

It can be advantageous that, prior to commencement of or during the acquisition of the raw medical data, the planning module takes into account the first reconstruction task resulting therefrom as well as the time of termination of the acquisition. This time instant and the maximum reconstruction time ensured by the guaranteed minimum performance define a period of time for which the planning module plans the assignment of the first reconstruction task to the computer group while taking into account further possible reconstruction tasks of further medical imaging devices that are still to be completed in the time period. Up to the commencement of the time period, the further reconstruction tasks may be subject to changes which can be taken into account by the planning module.

Furthermore, the planning module can take into account the chronological sequence of the time instants of the commencement and/or termination of the acquisition of the raw medical data to be processed by means of the first and the second medical imaging device. The knowledge of said time instants during the processing of raw medical data recorded by means of more than one medical imaging device can be used for example for prioritizing the tasks or for a better utilization of the capacities of the computer group.

The computing management computer is preferably designed such that the guaranteed minimum performance for the processing of raw medical data is ensured as a function of the capacity required for processing the raw medical data and/or as a function of technical characteristics of the interconnected computers. The guaranteed minimum performance therefore can be described by a parameter that can be specified on a variable basis. The dependence on technical characteristics of the computer group is advantageous, since in this way it is possible to guarantee a greater minimum performance for a computer group having a higher free capacity than for a computer group having a lower free capacity. Alternatively, if a first computer of the computer group that is assigned to the first medical imaging device is present, a minimum performance can be guaranteed for the first medical imaging device, which is characterized by maintaining that the minimum performance is ensured by the use of the first computer subject to the condition that no raw medical data acquired by means of a further medical imaging device is processed on said first computer.

In a preferred embodiment of the method, the computer group, the computing management computer and the medical imaging device are located within a clinical operations facility. The clinical facility can be in the form of one building or a buildings complex in which persons are examined for diseases or patients are treated and radiological examinations are carried out for this purpose. Medical imaging devices are used for the radiological examinations, and the devices and the associated computers, as well as the available software, are operated and controlled by medical personnel. Examples of this are hospitals and radiological practices. The advantage of such a clinical facility is that only medical personnel have access to the raw medical data and image data, which ensures that data privacy is guaranteed.

The invention further concerns a system having a computing management computer and at least one medical imaging device, which has an interface to a computer group composed of at least two computers that are connected to one another. In this case the at least one medical imaging device, the computer group and the computing management computer are designed to perform the method for reconstructing medical image data as described above. The advantages of the inventive system substantially correspond to the advantages of the inventive method, as explained in detail above. Features, advantages or alternative embodiments cited in this regard apply equally to the system.

The invention also encompasses a non-transitory, computer-readable data storage medium encoded with programming instructions that, when the storage medium is loaded directly into a memory of a programmable computer of the inventive system, cause the computer to perform the method for reconstructing medical image data as described above. In this case the programming instructions may possibly require program peripherals, e.g. libraries and help functions, in order to realize the corresponding embodiments of the method. The programming instructions can be software in the form of source code that still needs to be compiled and linked, or that only needs to be interpreted, or can be an executable software code that merely has yet to be loaded into a corresponding computing unit in order to execute.

BRIEF DESCRIPTION OF THE DRAWINGS

FIG. 3 is a flowchart of a second embodiment of the method according to the invention.

FIG. 4 is a flowchart of a third embodiment of the method according to the invention.

FIG. 5 is a flowchart of a fourth embodiment of the method according to the invention.

FIGS. 6a and 6b respectively are block diagrams of variants of a second embodiment, having a medical imaging device and a computer group, according to the invention.

FIG. 7 is a block diagram of an embodiment, having two medical imaging devices and a computer group, according to the invention.

DESCRIPTION OF THE PREFERRED EMBODIMENTS

Figure 1:
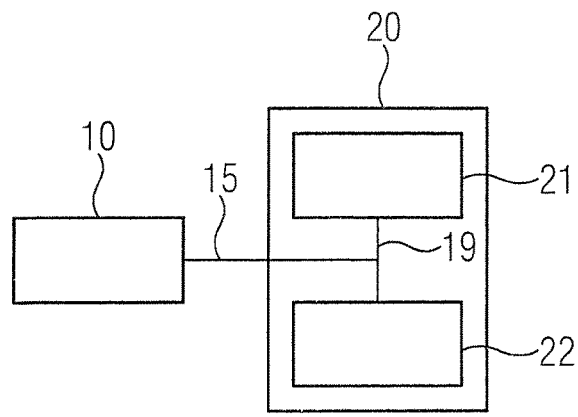
FIG. 1 is a block diagram of a first embodiment, having a medical imaging device and a computer group, according to the invention.

FIG. 1 shows a first embodiment of a method according to the invention, having a medical imaging device 10 and a computer group 20 composed of a computer 21 and a further computer 22, which are connected to one another via an interface 19. The computer group can have further computers. The medical imaging device 10 is connected to the computer group 20 via an interface 15.

The medical imaging device 10 is designed for generating a scan of an examination subject or a part thereof and for providing said scan in the form of images. The images can be presented on a display monitor and for example reproduce cross-sectional slice images from desired organs and can be used for diagnostic or therapeutic purposes. Medical personnel, in particular radiologists, can produce diagnoses on the basis of the images and initiate treatment methods. Examples of medical imaging devices are magnetic resonance scanners or X-ray machines. A computer 21 and a computer 22, as are combined in a computer group 20, are devices each featuring a processor, a working memory and a hard disk, and in a typical embodiment are computers.

Figure 2:
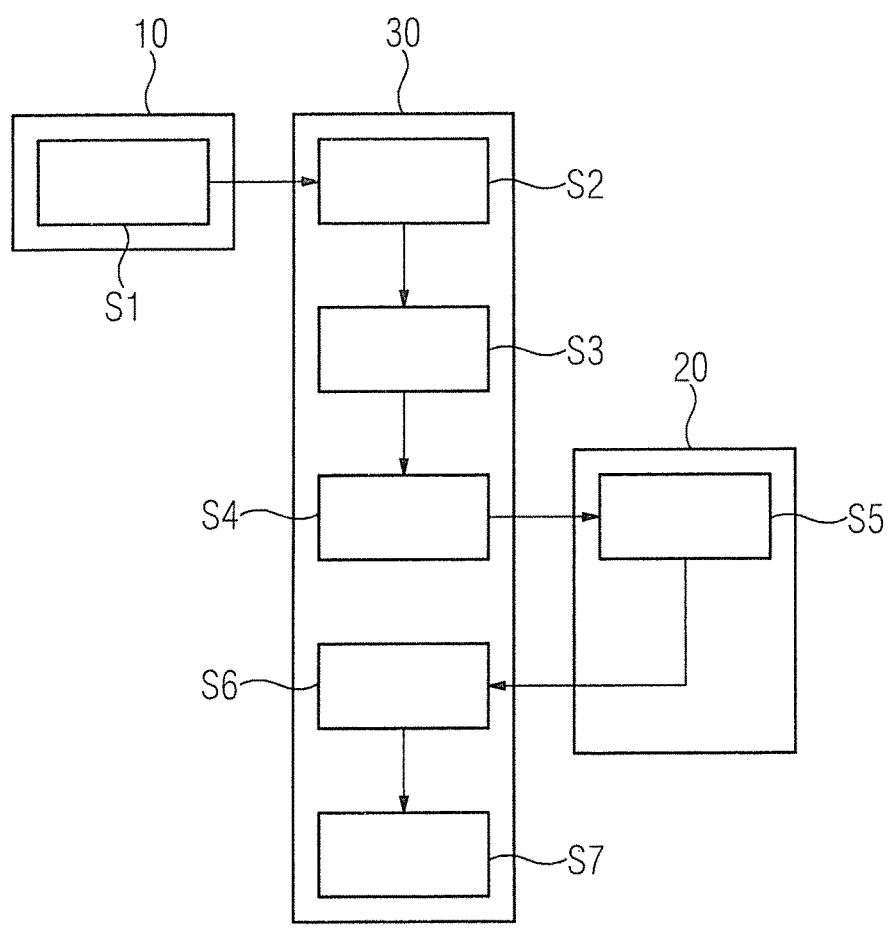
FIG. 2 is a flowchart of a first embodiment of the method according to the invention.

FIG. 2 shows a flowchart of the inventive method V1 for reconstructing medical image data. In a first method step S1, the medical imaging device 10 acquires raw medical data of an examination subject. In a further method step S2, a computing management computer 30 is provided which ensures that a guaranteed minimum performance is maintained and in method step S3 checks the free capacities of the computer group 20. In method step S4, the computing management computer 30 assigns the raw medical data to the computer group 20, which processes the raw medical data in method step S5. Next, in method step S6, the merging of the processed raw medical data to produce reconstructed medical image data is managed before the reconstructed medical image data is provided by the computing management computer 30 in method step S7.

FIG. 3 shows a flowchart of a second embodiment of an inventive method V2, wherein the second inventive method V2 is different from the first inventive method V1 in that when assigning the raw medical data to the computer group in method step S4', the computing management computer 30 follows the following course: In method step S4a', the raw medical data are divided into at least a first and a second data packet, each containing subsets of the raw medical data. Each data packet preferably also contains the information required for its processing, and the union set of the two data packets contains the raw medical data necessary for reconstructing the medical image data, which typically is all of the acquired raw medical data. In method step S4b', each data packet is assigned as a self-contained unit to a computer of the computer group 20 for processing. Preferably, the computing management computer 30 undertakes the subdivision into data packets in such a way that each data packet can be assigned to a different computer of the computer group 20, i.e. the computing management computer 30 for example assigns the first data packet to the computer 21 and the second data packet to the computer 22. The smaller the number of data packets, the fewer individual steps are necessary for subdividing the raw medical data and for merging the processed raw medical data. A smaller number of data packets during the processing while conforming to given boundary conditions such as the guaranteed minimum performance is accordingly preferred compared to a higher number. When subdividing the raw medical data into data packets, the computing management computer 30 takes into account the free capacities of the computers 21 and 22 of the computer group 20 and performs the subdivision accordingly. The division can also be effected into more than two data packets and/or the computer group 20 can comprise more than two computers. Generally, it is not necessary to assign a data packet to every computer in the computer group.

Method V2 also differs from method V1 in method step S5' in terms of the processing of the raw medical data 5. The processing of the raw medical data is still undertaken by the computer group 20, but the individual computers 21 and 22 of the computer group 20 are embodied for processing the two data packets.

FIG. 4 shows a flowchart of a third embodiment of an inventive method V3, wherein the third inventive method V3 is different from the first inventive method V1 in the manner in which the raw medical data is assigned to the computer group. In method V3, this method step S4" is characterized in that the computing management computer 30 is embodied to assign the raw medical data required for the reconstruction of a single medical image to precisely one computer 21 of the computer group 20. A single medical image typically relates to the medical image data reconstructed from the raw medical data that is acquired from precisely one examination subject. Alternatively, a single medical image can also relate to a subset of the medical image data that is reconstructed from the raw medical data of precisely one examination subject. The subset of the medical image data preferably shares a common feature, such as the slice orientation or the image contrast in magnetic resonance tomography, for example. The computing management computer 30 assigns the raw medical data to the computer 21, which has sufficient free capacity available and is embodied to perform the processing of the raw medical data in method step S5. Method V3 differs from method V2 in particular in that the division of the raw medical data into at least two data packets (method step S4a') is omitted.

FIG. 5 shows a flowchart of a fourth embodiment of an inventive method V4, wherein the fourth inventive method V4 is different from the first inventive method V1 in method steps S3 to S5. In method step S3', in addition to checking the free capacities of the computer group 20, the computing management computer 30 also checks how the assignment of the raw medical data can be performed. The first option is to assign the raw medical data to the computer 21 of the computer group 20 according to method step S4", and the second option is to divide the raw medical data into two data packets according to method step S4a' and to assign the data packets to different computers 21 and 22 of the computer group 20 according to method step S4b'. The computing management computer 30 can decide between the two options in method step S3' and assign the raw medical data accordingly. Depending on the decision, in the case of the first option the raw medical data is processed on a computer 21 of the computer group 20 according to method step S5 or in the case of the second option on a plurality of computers of the computer group 20 according to method step S5'.

FIG. 6a and FIG. 6b schematically represent a second embodiment of an inventive method. In a first variant (FIG. 6a), the medical imaging device 10 and the computer group 20, composed of a first computer 23 and a further computer 24, are connected to one another via the interface 18. The medical imaging device 10 is connected to the first computer 23 via an interface 17, the first computer 23 being connected to the computer 24 of the computer group 20 via the interface 18. There is thus a direct connection between the medical imaging device 10 and the first computer 23. This embodiment is typically given when the first computer 23 is a reconstruction computer of the medical imaging device 10 which handles the latter's reconstruction tasks when the computer group 20 and/or the computing management computer 30 are not available according to the inventive method. The medical imaging device 10 can additionally be connected to the computer group 20 via a further interface 15. The computer group can comprise further computers. These computers can all be interconnected via interface 18 and/or be connected directly or indirectly to one another via a number of interfaces. In another variant, an indirect connection exists between the computer 23 and a computer 25 (FIG. 6b), for example when the computers 23, 24 and 25 are part of the computer group 20 and the computer 23 is connected to the computer 24 via the interface 18, computer 24 is connected to computer 25 via a further interface, but no interface exists between computers 23 and 25.

FIG. 7 schematically represents a third embodiment of an inventive method, comprising two medical imaging devices 10 and 11 and a computer group 20, composed of the computer 21 and the further computer 22, which are connected to one another via the interface 19. The medical imaging device 10 is connected to the computer group 20 via the interface 15, and the medical imaging device 11 via an interface 16. Further medical imaging devices can be connected to the computer group 20, in which case the computing management computer 30 is able to manage the processing of the raw medical data acquired by means of all of the medical imaging devices.

In summary, the invention concerns a method for reconstructing medical image data that has access to free capacities of at least two computers and manages the use thereof for the purposes of the reconstruction. The method provides a particularly reliable alternative to the reconstruction of medical image data based on algorithms that would require a working memory of above-average size.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for reconstructing medical image data, comprising: operating a medical imaging scanner to acquire raw medical data of an examination subject; providing said raw medical data from said medical imaging scanner, via an interface, to a computer group comprising a plurality of computers; placing a computing management computer in communication with said computer group and in communication with said medical imaging apparatus; with said computing management computer defining a minimum performance for reconstructing medical image data from a totality of said raw medical data; with said computing management computer, if a computer in said computer group is assigned directly to said medical imaging scanner, automatically defaulting to assign said reconstructing to said computer that is assigned directly to said medical imaging scanner; with said computing management computer, if no computer in said computer group is assigned directly to said medical imaging scanner, automatically checking respective free capacities, with respect to said minimum performance, of the computers of said computer group before assigning the raw medical data to a computer in said computer group for said reconstructing; and with said computing management computer, automatically managing distribution of the raw medical data among said computers in said computer group in order to reconstruct a totality of said medical image data from said totality of raw medical data in multiple, different computers in said computer group each having a free capacity that maintains said minimum performance; with said computing management computer, automatically implementing said managing of said distribution of the raw medical data among the computers in said computer group by dividing the raw medical data into a plurality of data packets, with each of said data packets containing a subset of said raw medical data and including, in each data packet, all information needed to reconstruct image data from the subset of raw medical data in that respective data packet, thereby making each data packet a self-contained unit; assigning the respective data packets as said self-contained units to different computers of the computer group, and managing respective reconstructions of the respective data packets by respective individual computers of said computer group dependent on at least three factors selected from the group consisting of matching the data packets to respective capacities of the computers of the computer group according to processing requirements of the respective partial reconstructions, apriority assigned to the reconstruction of the medical image data, a number of examination subjects for which raw medical data are available, a number medical imaging apparatuses from which the raw medical data were acquired, a raw data acquisition method by which the raw medical data were acquired, and a number of computers in said computer group, each reconstruction by each of said respective individual computers being a partial reconstruction of said totality of medical image data; with said computing management computer, combining the respective partial reconstructions performed by said multiple, different computers in said computer group to form a complete set of reconstructed medical image data; and making the complete set of reconstructed medical image data available in electronic form, as a datafile from said computer group or from said computing management computer.

2. A method as claimed in claim 1 comprising, with said computing management computer, assigning the raw medical data required for reconstruction of a single medical image to a single computer of said computer group, and reconstructing the raw medical data to produce said single medical image with said single computer.

3. A method as claimed in claim 1 wherein said computer assigned directly to said medical imaging scanner is a first computer, and comprising, with said computing management computer, assigning no raw medical data to said first computer if and while said first computer is processing raw medical data of said medical imaging apparatus.

4. A method as claimed in claim 1 wherein said computer assigned directly to said medical imaging scanner is a first computer, and comprising, with said computing management computer, interrupting reconstructing of said raw medical data, assigned to said first computer, by said first computer if a capacity of said first computer is required for reconstructing additional raw medical data from said medical imaging apparatus and, with said computing management computer, then implementing said checking and continuing reconstructing of said raw medical data, which was interrupted in said first computer, by said multiple, different computers of said computer group or with said first computer after said first computer has completed reconstructing of the further raw medical data, in order to guarantee said minimum performance.

5. A method as claimed in claim 1 wherein said computing management computer comprises a planning processor and, with said planning processor, prior to commencing acquisition of said raw medical data with said medical imaging device:
    implementing said checking of said free capacities of the computers of the computer group; and
    specifying a subsequent assignment to respective computers of said computer group after acquisition of said raw medical data has been completed by said medical imaging apparatus.

6. A method as claimed in claim 5 comprising, with said planning processor, specifying said subsequent assignment dependent on a time at which the acquisition of said raw medical data is expected to be completed by said medical imaging apparatus.

7. A method as claimed in claim 1 wherein said medical imaging apparatus is first medical imaging apparatus and said interface is a first interface, and said method comprising:
    placing a second medical imaging apparatus in communication with said computer group via a second interface;
    operating said second medical imaging apparatus to acquire further raw medical data of an examination subject;
    providing said raw medical data from said second medical imaging apparatus to said computing management computer; and
    with said computing management computer, also assigning said further raw medical data acquired by said second medical imaging apparatus to said computer group for said reconstructing together with or in parallel with said raw medical data from said first medical imaging apparatus in order to guarantee said minimum performance.

8. A method as claimed in claim 7 comprising providing said second medical imaging apparatus as an apparatus that operates according to an imaging modality that differs from an imaging modality of said first medical imaging apparatus.

9. A method as claimed in claim 7 wherein said computing management computer comprises a planning processor and, with said planning processor, prior to commencing acquisition of said raw medical data and said further raw medical data:
    checking free capacities of the computers of the computer group;
    specifying a subsequent assignment of the raw medical data and the further raw medical data to respective computers of the computer group after acquisition of said raw medical data and said further raw medical data; and
    specifying said subsequent assignment dependent on at least one of a chronological sequence of respective commencement of acquisition of said raw medical data and commencement of acquisition of said further raw medical data, and respective terminations of acquisition of said raw medical data and further raw medical data.

10. A method as claimed in claim 1 comprising wherein said minimum performance is a function of at least one of a capacity required for processing said raw medical data, and technical characteristics of the respective computers in said computer group.

11. A method as claimed in claim 1 comprising situating said computer group, said computing management computer and said medical imaging apparatus within a single clinical operations facility.

12. A medical data acquisition and processing system, comprising: a medical imaging scanner configured to acquire raw medical data of an examination subject; a computer group comprising a plurality of computers provided, via an interface, with said raw medical data from said medical imaging scanner; a computing management computer in communication with said computer group and in communication with said medical imaging apparatus; said computing management computer being configured to define a minimum performance for reconstructing medical image data from a totality of said raw medical data; said computing management computer, if a computer in said computer group is assigned directly to said medical imaging scanner, being configured to automatically default to assign said reconstructing to said computer that is assigned directly to said medical imaging scanner; if no computer in said computer group is assigned directly to said medical imaging scanner, said computing management computer being configured to automatically check respective free capacities, with respect to said minimum performance, of the computers of said computer group before assigning the raw medical data to a computer in said computer group for said reconstructing; and said computing management computer being configured to automatically manage distribution of the raw medical data among said computers in said computer group in order to reconstruct a totality of said medical image data from said totality of raw medical data in multiple, different computers in said computer group each having a free capacity that maintains said minimum performance; said computing management computer being configured to automatically implement said managing of said distribution of the raw medical data among the computers in said computer group by dividing the raw medical data into a plurality of data packets, with each of said data packets containing a subset of said raw medical data and including, in each data packet, all information needed to reconstruct image data from the subset of raw medical data in that respective data packet, thereby making each data packet a self-contained unit; said computing management computer being configured to assign the respective data packets as said self-contained units to different computers of the computer group, and managing respective reconstructions of the respective data packets by respective individual computers of said computer group dependent on at least three factors selected from the group consisting of matching the data packets to respective capacities of the computers of the computer group according to processing requirements of the respective partial reconstructions, a priority assigned to the reconstruction of the medical image data, a number of examination subjects for which raw medical data are available, a number medical imaging apparatuses from which the raw medical data were acquired, a raw data acquisition method by which the raw medical data were acquired, and a number of computers in said computer group, each reconstruction by each of said respective individual computers being a partial reconstruction of said totality of medical image data; said computing management computer being configured to combine the respective partial reconstructions performed by said multiple, different computers in said computer group to for a complete set of reconstructed medical image data: and said computing management computer being configured to make the complete set of reconstructed medical image data available in electronic form, as a datafile from said computer group or from said computing management computer.

13. A non-transitory, computer-readable data storage medium encoded with programming instructions, said storage medium being distributively loaded into a computing management computer and computers in a computer group comprising a plurality of computers of a system that also comprises a medical imaging scanner that produces raw medical data, said programming instructions causing said computing management computer to: define a guaranteed minimum performance for reconstructing medical image data from a totality of said raw medical data; if a computer in said computer group is assigned directly to said medical imaging scanner, automatically default to assign said reconstructing to said computer that is assigned directly to said medical imaging scanner; if no computer in said computer group is assigned directly to said medical imaging scanner, automatically check respective free capacities of the computers of said computer group before assigning the raw medical data to a computer of said computer group for said reconstructing; and automatically manage distribution of the raw medical data among said computers in said computer group in order to reconstruct a totality of said medical image data from said totality of raw medical data in multiple, different computers in said computer group each having a free capacity that maintains said minimum performance; automatically implement said managing of said distribution of the raw medical data among the computers in said computer group by dividing the raw medical data into a plurality of data packets, with each of said data packets containing a subset of said raw medical data and including, in each data packet, all information needed to reconstruct image data from the subset of raw medical data in that respective data packet, thereby making each data packet a self-contained unit; assign the respective data packets as said self-contained units to different computers of the computer group, and managing respective reconstructions of the respective data packets by respective individual computers of said computer group dependent on at least three factors selected from the group consisting of matching the data packets to respective capacities of the computers of the computer group according to processing requirements of the respective partial reconstructions, a priority assigned to the reconstruction of the medical image data, a number of examination subjects for which raw medical data are available, a number medical imaging apparatuses from which the raw medical data were acquired, a raw data acquisition method by which the raw medical data were acquired, and a number of computers in said computer group, each reconstruction by each of said respective individual computers being a partial reconstruction of said totality of medical image data; combine the respective partial reconstructions performed by said multiple, different computers in said computer group to form a complete set of reconstructed medical image data; and make the complete set of reconstructed medical image data available in electronic form, as a datafile from said computer group or from said computing management computer.

* * * * *